(12) United States Patent
Winner

(10) Patent No.: US 6,894,208 B2
(45) Date of Patent: May 17, 2005

(54) MARIGOLD HYBRID 50011

(75) Inventor: Blair Winner, Ventura, CA (US)

(73) Assignee: Ball Horticultural Company, West Chicago, IL (US)

( * ) Notice: Subject to any disclaimer, the term of this patent is extended or adjusted under 35 U.S.C. 154(b) by 184 days.

(21) Appl. No.: 09/922,139

(22) Filed: Aug. 3, 2001

(65) Prior Publication Data
US 2002/0120965 A1 Aug. 29, 2002

Related U.S. Application Data

(60) Provisional application No. 60/223,023, filed on Aug. 4, 2000, and provisional application No. 60/225,934, filed on Aug. 17, 2000.

(51) Int. Cl.$^7$ .............................. A01H 5/00; A01H 1/00; C12N 5/00
(52) U.S. Cl. ..................... 800/323.1; 800/260; 435/410
(58) Field of Search .............................. 800/323.1, 260, 800/323; 435/410

(56) References Cited

FOREIGN PATENT DOCUMENTS

| FR | 2 740 656 A | 5/1997 |
|---|---|---|
| WO | WO 00 32788 A | 6/2000 |

OTHER PUBLICATIONS

Principles of Cultivar Development vol. 1 Theory and Technique. Walter R. Fehr 1987.*
Clemson Extension Home & garden information center Marigold. Karen Russ and Bob Polomski. Mar. 1998.*
"Xanthophyll Marigolds" Pan American Seed (1998).
Ball Red Book, 15$^{th}$ edition, George J. Ball Publishing (1991) pags. 662–665.
Hortus Third A Concise Dictionary of Plants Cultivated in the United States and Canada, MacMillan Publishing Company (1976).
B. Singh and V. Swarp, Indian Journal of Genetics& Plant Breeding, 33(2): 172–175 (1973).

K. Anuradha et al, Indian Journal of Horticulture, 47(3): 353–357 (1990).
R. Piccaglia et al., Industrial Crops and Products, 8: 45–51 (1998).
D. Balnave et al, Asian–Australiasian Journal of Animal Sciences 9(5): 515–517 (1996).
"Carotenoids as Colorants and Vitamin A Precursors—Technological and Nutritional Applications" Edited by J. Christopher Bauernfeind, Academic Press, pp. 836–838 (1981).
Xanthophyll Marigolds; Pan American Seed (2001).
Muni Ram, et al.: Plant Population and Yields in *Tagetes patula* and *Tagetes erecta*:; Database accession No. 2001:38956; XP002214399; abstract & Journal of Herbs, Spices & Medicinal Plants. (2000) vol. 7, No. 3, PP. 1–5. 4 Ref. ISSN: 1049–6475.
Misra Pratibha et al: "In vitro maintenance of F1 hybrid." Database accession No. PREV200000375054; XP00221440 abstract & Current Science (Bangalore), vol 78, No. 4, 2000, pp. 383–384, ISSN: 0011–3891.
Vereecke, M.: "Comparative study of some new F1 gybrids of *Tagetes erects*"; Database accession No. 74:10869 CABA; XP002214401 abstract & Mededelingen Van De Faculteit Landbouwwetenschappen, Rijksuniversiteit Gent, (1973) vol. 38, No. 2, PP. 577–589 9 Ref. ISSN: 0368–9697.
Arora, J.S., et al.: "Performance of marigold cutivars under North Indian conditions" Database Accession No. 81:14360 CABA XP002214402 abstract & (1980) PP. 81–82. 1 Ref. Publisher: Tamil Nadu Agricultural University Coimbatore Meeting Info.: Nationa Seminar on Production Technology for Commerical Flower Cropers.
International Search Report dated Oct. 10, 2002.

* cited by examiner

*Primary Examiner*—Bruce R. Campell
*Assistant Examiner*—Annette H Para
(74) *Attorney, Agent, or Firm*—Wood, Phillips, Katz, Clark & Mortimer

(57) ABSTRACT

The present invention relates to a new and distinct hybrid of marigold referred to as *Tagetes erecta* 50011.

10 Claims, 2 Drawing Sheets

US 6,894,208 B2

MARIGOLD HYBRID 50011

RELATED APPLICATION INFORMATION

This application claims priority from U.S. Ser. No. 60/223,023, filed on Aug. 4, 2000 and U.S. Serial No. 60/225,934 filed on Aug. 17, 2000.

FIELD OF THE INVENTION

The present invention relates to a new and distinct hybrid of marigold, *Tagetes erecta*, which is referred to as 50011. Marigold hybrid 50011 exhibits high xanthophyll production and high flower-weight yield. Additionally, 50011 exhibits male sterility and has fully-double flowers.

The present invention also relates to seed, pollen, cuttings and ovules of marigold hybrid 50011. Moreover, the present invention also relates to a tissue culture comprising regenerable cells of marigold hybrid 50011.

The present invention also relates to methods for producing $F_1$ hybrid marigold seed using marigold plant 50011 in breeding as a female parent. The present invention also relates to a $F_1$ hybrid or later generation marigold plants grown from the hybrid marigold seed produced by the aforementioned methods.

BACKGROUND OF THE INVENTION

The *Tagetes* genus is a member of the family Asteraceae, alternatively known as Compositae, and comprises some thirty species of strongly scented annual or perennial herbs. *Tagetes* are native from Arizona and New Mexico to Argentina (*Hortus Third A Concise Dictionary of Plants Cultivated in the United States and Canada*, Macmillan Publishing Company (1976)). Cultivated genera include *Tagetes erecta* commonly referred to as African marigold, *Tagetes patula* or the French marigold, *Tagetes erecta x patula* also known as the triploid marigolds, and *Tagetes tenuifolia* also known as *Tagetes signata* and signet marigold. Cultivated marigolds possess showy flowers and are useful for bedding, pots and cutting purposes (*Ball Red Book*, 15$^{th}$ edition, George J. Ball Publishing (1991)).

In addition to having ornamental value, the genus is recognized as a source for natural color, essential oils and thiophenes, which have nematicide properties. The pigmentation efficiency of marigold is of value in the poultry industry. Dried marigold petals and marigold petal concentrates are used as poultry feed additives to intensify the yellow color of egg yolks and broiler skin (R. Piccalia, M. Marotti, and S. Grandi, *Industrial Crops and Products*, 8:45–51 (1998)). The carotenoids desired in poultry tissues are a function of their dietary concentration, because poultry do not have the ability to synthesize carotenoids de novo. (D. Balnave and J. N. Bird, *Asian-Australiasian Journal of Animal Sciences*, 9 (5): 515–517 (1996)). The pigmenting ability of marigold petal meal resides largely in the carotenoid fraction known as the xanthophylls, primarily lutein esters (R. Piccalia, M. Marotti, and S. Grandi, *Industrial Crops and Products*, 8:45–51 (1998)).

For the feed additive industry, marigolds are produced primarily in Mexico, Peru, Africa, India, China and Thailand. 'Orangeade', commercially available from Pan American Seed Company, 622 Town Road, West Chicago, Ill. 60185, was one of the original xanthophyll varieties. Commercial improvements of 'Orangeade' include 'Deep Orangeade' and 'Scarletade'. 'Deep Orangeade' has lower flower yield than 'Orangeade', but greater than 'Scarletade'. 'Deep Orangeade' has greater xanthophyll production per hectare than 'Orangeade' due to more double flowers, but has reduced xanthophyll concentrations compared to 'Scarletade'. Current varieties used for xanthophyll production are open-pollinated and are either semi-double or segregate for fully-double flowers. Marigold hybrid 50011 of the present invention is the first fully-double commercial xanthophyll hybrid. Marigold 50011 has larger flowers and more vigor than 'Scarletade', yielding more grams of xanthophyll pigment per hectar. Future variety improvements beneficial for the feed additive industry include increased xanthophyll concentration, disease tolerance, improved vigor as well as the development of varieties that can be produced under different day lengths.

Both genetics and nutrition have been shown to effect marigold flower production. A report on the inheritance of quantitative traits of African marigold, identified that dominance and epistasis, the interaction between two non-allelic genes, had a major role in the inheritance of days for first flowering and flower weight. Additive gene effects and epistasis were found to be more predominant in inheritance of seasonal flower number (B. Singh and V. Swarp, *Indian Journal of Genetics & Plant Breeding*, 33(2):172–175 (1973)). In a nutritional study, increased nitrogen and phosphorus, both tested to levels of 90 kg/hectare, were shown to increase the yield of flowers and reduce the time to flower (K. Anuradha et al., *Indian Journal of Horticulture*, 47(3): 353–357 (1990)).

SUMMARY OF THE INVENTION

The present invention relates to a new and distinct hybrid of marigold, *Tagetes erecta*, which is referred to as 50011. The present invention also relates to seed, pollen, ovules and cuttings from said marigold plant. Moreover, the present invention relates to a tissue culture comprising regenerable cells marigold plant 50011.

The present invention also relates to seed of a marigold plant 50011 and to marigold plants produced by growing said seed.

The present invention also relates to a method of producing a first generation ($F_1$) hybrid marigold seed. The method involves crossing a first parent marigold plant with a second and different parent marigold plant and harvesting the resultant first generation ($F_1$) hybrid marigold seed. Either the first or second marigold parent plant can be the female parent plant and can be marigold plant 50011. Additionally, the present invention also relates to a hybrid or inbred marigold plant produced by growing the hybrid seed produced by said method.

The present invention also relates to a marigold plant having a lineage which includes marigold plant 50011 and which exhibits at least one of the following characteristics: a high xanthophyll production (grams of xanthophyll per plant), high flower-weight yield (grams of flowers per plant), male sterility and fully-double flowers.

Finally, the present invention relates to viable marigold seeds and plants and succeeding generations thereof which are grown from seeds deposited under ATCC Accession number PTA-2100.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
FIG. 1 is a color photograph of marigold hybrid 50011 inflorescence.
Figure 2:
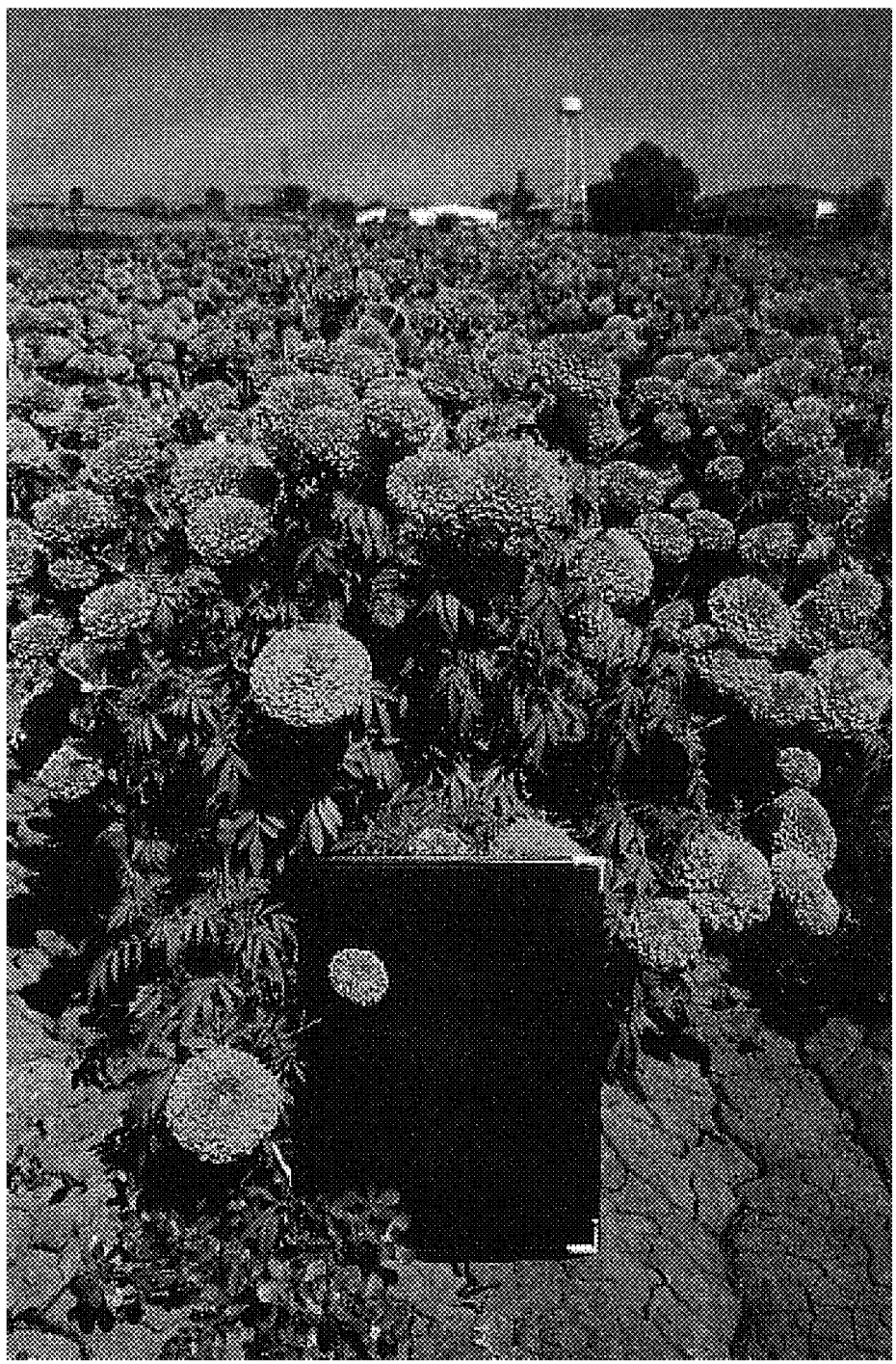
FIG. 2 is a color photograph of marigold hybrid 50011 plants.

The present invention relates to a new and distinct hybrid of marigold, *Tagetes erecta*, which is referred to herein as 50011.

Marigold hybrid 50011 arose from breeding and research efforts at Pan American Seed Company in Santa Paula, Calif. In January of 1995, a cross was made between a first Pan American marigold inbred breeding line as a female parent and a second Pan American marigold inbred breeding line as the male parent and the resulting seeds were collected. In April 1995, seeds were germinated and in July 1995, plant 50011 was identified as a superior hybrid from the flowering progeny.

50011 possess a number of unique characteristics. Specifically, 50011 exhibits: high xanthophyll production (grams of xanthophyll per plant), high flower-weight yield (grams of flowers per plant), male sterility and fully-double flowers.

50011 is genetically stable and can be stably reproduced by means of asexual propagation. Samples of 50011 thus far tested have been found to be stable through asexual propagation. Cuttings for asexual propagation can be taken at any time of the year and no special hormones or soil mixtures are required.

50011 maintains functional female organs, and can thus be employed as a female parent in traditional plant breeding. Pollen production can be observed under stress conditions. Specifically, 50011 can be used in crosses with other marigold varieties possessing commercially desirable phenotypes or as the female parent to produce new marigold varieties. Therefore, the present invention contemplates a marigold plant having a lineage which includes marigold plant 50011 and which exhibits one or more of the following characteristics: high xanthophyll production, high flower-weight yield, male sterility and/or fully-double flowers.

50011 has not been observed under all possible environmental conditions. The phenotype may vary significantly with variations in environment such as temperature, light intensity and day length, without, however, any variance in genotype.

The following examples are set forth as representations of specific and preferred embodiments of the present invention. These examples are not to be construed as limiting the scope of the invention in any manner. It should be understood that many variations and modifications can be made while remaining within the spirit and scope of the invention.

EXAMPLE 1

Description of Marigold Hybrid 50011

The below determinations were made in Santa Paula, Calif. on mature plants.

Plant Dimensions:
  Width: minimum of about 50 cm maximum of about 90 cm
  Height: minimum of about 50 cm maximum of about 95 cm
Flower:
  Fully-double flowers from about 7.0 cm to about 12.0 cm in diameter
Flower Color:
  about RHS Yellow-Orange Group 23A (However, flower color can fluctuate depending upon maturity and growing conditions).

EXAMPLE 2

Comparison of Flower Yield and Pigment Concentration of Marigold Hybrid 50011 with 'Searletade' and 'Orangeade'

In 1999, a field trial was conducted at Pan American Seed in Santa Paula, Calif. Total flower yields were calculated for ten plants at five harvest intervals throughout the growing season.

Total xanthophyll content was calculated from lutein and zeaxanthin concentration as determined by high performance liquid chromatography (hereinafter "HPLC") analysis for four flower harvests. For the analysis, six flower heads from each of four harvests were silaged, ground and lyophilized. Xanthophylls were extracted from dried marigold meal using a modified extraction protocol including saponification (*Carotenoids as Colorants and Vitamin A Precursors Technological and Nutritional Applications*, Academic Press (1981)).

HPLC equipment consisted of a Waters Photodiode Array 996 detector, a 600E pump, and a 712 WISP (Waters Corporation, 34 Maple Street, Milford, Mass. 01757). Separation was obtained with a YMC Carotenoid reverse phase column, 5-micron, 4.6×250 mm with a guard column of the same material (Waters Corporation, 34 Maple Street, Milford, Mass. 01757). The mobile phase was prepared using HPLC grade solvents and degassed with helium. The solvents were pumped separately to give a final: 81% methanol, 4% water, and 15% tetrahydrofuran stabilized with 0.2% BHT. Xanthophylls were separated isocratically at 30° C. with a flow rate of 1.7 ml/minute. Lutein typically eluted at 6.8 minutes and zeaxanthin at 8.0 minutes. The Photodiode array was set to scan between 280 nm and 520 nm to confirm spectral identity and the peak responses were measured at 445 nm. After sample extraction, 2 ml was dried under nitrogen. For HPLC analysis, the dried samples were resuspended in 20 $\mu$l tetrahydrofuran and then brought up to 2 ml with methanol. The samples were filtered through a 0.45$\mu$ filter and placed in a brown glass vial. For both samples and standards 50 $\mu$l were injected. HPLC standards were obtained from ICC Indofine Chemicals, New Jersey and dissolved in a small amount of THF, then diluted in ethanol to give working standards between 30 $\mu$l/ml and 0.1 $\mu$g/ml.

Table 1 compares data for flower yield and xanthophyll production for marigold hybrid 50011, and 'Scarletade' and 'Orangeade'. Cultivars 'Scarletade' and 'Orangeade' are commercially produced for the xanthophyll industry and are available from PanAmerican Seed Company, 622 Town Road, West Chicago, Ill. 60185. Marigold hybrid 50011 of the present invention had the highest total flower yield of the three cultivars tested. The total xanthophyll concentration based on lutein and zeaxanthin was lower than 'Scarletade' and higher than 'Orangeade'. On a per hectare basis, hybrid 50011 would yield the highest level of total xanthophyll when compared with 'Scarletade' and 'Orangeade'.

TABLE 1

| Variety | Average Flower Yield per Plant (kg) | Average Total Xanthophyll Production per Harvest (g/kg fresh weight) | Average Total Xanthophyll per Plant (g) |
|---|---|---|---|
| Hybrid 50011 | 2.09 | 1.71 +/− 0.45 | 3.57 |
| 'Scarletade' | 1.66 | 1.86 +/− 0.33 | 3.09 |
| 'Orangeade' | 1.22 | 1.23 +/− 0.43 | 1.5 |

Deposit Information

Two thousand five hundred seeds (2500) of *Tagetes erecta* hybrid 50011 disclosed above and recited in the appended claims have been placed on deposit with the American Type Culture Collection (ATCC), 10801 University Blvd., Manassas, Va., 20110-2209 under Deposit Accession Number PTA-2100 on Jun. 16, 2000. This deposit was made in compliance with the Budapest Treaty requirements that the duration of the deposit should be for thirty (30) years from the date of the deposit or for five (5) years after the last request for the deposit at the depository or for the enforceable life of a U.S. Patent that matures from this application, whichever is longer. These marigold seeds will be replenished should it become non-viable during that period at the depository.

All references cited herein are incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

What is claimed is:

1. Hybrid marigold seed designated 50011, wherein a sample of said seed has been deposited under ATCC Accession No. PTA-2100.

2. A marigold plant or parts thereof, produced by growing the seed of claim 1.

3. Pollen of the plant of claim 2.

4. An ovule or ovules of the plant of claim 2.

5. A cutting of the plant of claim 2.

6. A marigold plant, or its parts, having all the physiological and morphological characteristics of marigold 50011, wherein a sample of seed has been deposited under ATCC Accession No. PTA-2100.

7. A tissue culture of regenerable cells of a marigold plant of claim 2 wherein the tissue culture regenerates a plant capable of expressing all the physiological and morphological characteristics of marigold plant 50011 and further wherein a sample of said seed has been deposited under ATCC Accession No. PTA-2100.

8. A marigold plant, or its parts, regenerated from the tissue culture of claim 7 and capable of expressing all the morphological and physiological characteristics of hybrid marigold plant 50011, a sample of said seed having been deposited under ATCC Accession No. PTA-2100.

9. A method for developing a marigold plant in a marigold breeding program using plant breeding techniques which include employing a marigold plant, or its parts, as a source of plant breeding material comprising, using the marigold plant, or its parts, of claim 2 as a source of said breeding materials.

10. A method for producing marigold seed, the method comprising the step of crossing the plant of claim 2 with another, different marigold plant.

* * * * *